United States Patent
Abraham-Fuchs et al.

(10) Patent No.: US 9,301,709 B2
(45) Date of Patent: Apr. 5, 2016

(54) METHOD FOR OPTIMIZING THE GAS CONVERSION RATE IN A RESPIRATORY GAS ANALYZER

(75) Inventors: Klaus Abraham-Fuchs, Erlangen (DE); Maximilian Fleischer, Höhenkirchen (DE); Karsten Hiltawsky, Schwerte (DE); Oliver Hornung, Fürth (DE); Thomas Krüger-Sundhaus, Pommersfelden (DE); Erhard Magori, Feldkichen (DE); Roland Pohle, Ottenhofen (DE); Oliver Von Sicard, München (DE)

(73) Assignee: Robert Bosch GmbH, Stuttgart (DE)

( * ) Notice: Subject to any disclaimer, the term of this patent is extended or adjusted under 35 U.S.C. 154(b) by 704 days.

(21) Appl. No.: 12/890,834

(22) Filed: Sep. 27, 2010

(65) Prior Publication Data

US 2011/0077544 A1    Mar. 31, 2011

(30) Foreign Application Priority Data

Sep. 28, 2009    (DE) .......................... 10 2009 043 222

(51) Int. Cl.
*A61B 5/08*    (2006.01)
(52) U.S. Cl.
CPC ...................... *A61B 5/082* (2013.01)
(58) Field of Classification Search
CPC ....................................... A61B 5/082

USPC ................... 600/529, 532, 537, 543; 60/277; 423/235, 239.1
See application file for complete search history.

(56) References Cited

U.S. PATENT DOCUMENTS

| | | | |
|---|---|---|---|
| 7,624,628 B2 * | 12/2009 | Bartley | 73/114.75 |
| 2003/0023182 A1 * | 1/2003 | Mault et al. | 600/532 |
| 2003/0046924 A1 * | 3/2003 | Iihoshi et al. | 60/277 |
| 2004/0000135 A1 * | 1/2004 | Uchida | 60/277 |
| 2004/0133116 A1 * | 7/2004 | Abraham-Fuchs et al. | 600/532 |

FOREIGN PATENT DOCUMENTS

WO    WO 2008052104 A2    5/2008

OTHER PUBLICATIONS

American Thoracic Society Documents; ATS/ERS Recommendations for Standardized Procedures for the Online and Offline Measurement of Exhaled Lower Respiratory Nitric Oxide and Nasal Nitric Oxide, American Thoracic Society (ATS) and the European Respiratory Society (ERS) 2005; Others; 2005;.

* cited by examiner

*Primary Examiner* — Jacqueline Cheng
*Assistant Examiner* — Tho Tran
(74) *Attorney, Agent, or Firm* — Maginot, Moore & Beck LLP

(57) ABSTRACT

A method for optimizing a gas conversion rate in a respiratory gas analyzer, more particularly for nitric oxide (NO) in the respiratory gas, and an associated device are disclosed.

18 Claims, 1 Drawing Sheet

METHOD FOR OPTIMIZING THE GAS CONVERSION RATE IN A RESPIRATORY GAS ANALYZER

PRIORITY STATEMENT

The present application hereby claims priority under 35 U.S.C. §119 on German patent application number DE 10 2009 043 222.1 filed Sep. 28, 2009, the entire contents of which are hereby incorporated herein by reference.

FIELD

At least one embodiment of the present invention generally relates to a method for optimizing a gas conversion rate in a respiratory gas analyzer, more particularly for nitric oxide (NO) in the respiratory gas, and to an associated device.

BACKGROUND

In some gas sensor applications, it is necessary before the measurement to convert the gas analyte into another product that is detectable by the sensor. Reasons for this can e.g. lie in the characteristic of the sensor, if it cannot detect the original target gas, or e.g. lie in increasing the specificity of the measurement, if the specificity of a sensor is lower for the original target gas than the specificity of the same (or another) sensor for the converted target gas. It is precisely in the detection of individual gasses in a complex gas mixture (such as the human exhaled air) that the specificity or cross-sensitivity of the sensor plays a decisive role.

Very small amounts of nitric oxide (nitrogen monoxide, NO) are continuously released into the respiratory gas flow from the cells of the airways. NO constitutes an important marker for the diagnosis and optimized therapy of asthma and other inflammatory airway diseases. With a prevalence of approximately 5% of adults and approximately 20% of children in developed industrial nations, asthma is one of the most prevalent diseases. In inflammatory processes of the airways, e.g. asthma, there are elevated NO concentrations of 40 ppb (parts per billion) and more in the exhaled air. Imminent asthma attacks can be recognized significantly earlier from an increase in the NO content of the exhaled air than from a lung-function test, which ultimately only quantifies a symptomatic narrowing of the bronchi. Thus, the NO measurement in the exhaled air is a preferred method for diagnosing and monitoring the therapy progress of asthma and other inflammatory airway diseases.

Cost-effective NO sensors with the required sensitivity in the ppb range have until now not been commercially available. A newly developed $NO_2$ sensor based on "suspended gate FET" technology meets the aforementioned requirements. However, a conversion module for converting the NO in the respiratory gas into $NO_2$, which can be detected by the sensor, must be placed upstream of such a sensor. Ideally, such a conversion module should hold for a number of months or even years, be cost-effective and convert NO into $NO_2$ at a very high conversion rate, which is constant.

Nitrogen monoxide is converted to nitrogen dioxide as per the following reaction equation:

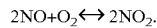

Nitrogen monoxide can be converted to nitrogen dioxide in a respiratory gas sensor instrument by an arrangement for oxidizing nitrogen monoxide to nitrogen dioxide, for example by guiding the (respiratory) air through an oxidizing agent (e.g. potassium permanganate, perchlorate salts or the like) or another oxidation catalyst.

The fact that $NO_2$ is significantly more soluble in water than NO constitutes another problem. Therefore, a method is required for keeping the concentration of the converted $NO_2$ as constant as possible and quantitatively measurable in the moist respiratory gas. As a result of the higher solubility of $NO_2$ in water, part of the (converted) $NO_2$ is dissolved in water in (respiratory) air with a high moisture content, the concentration of the measurable $NO_2$ drops and a seemingly too low $NO_2$ and, respectively, NO content is measured.

If it is possible to convert the NO in the respiratory air into $NO_2$ in a reliable and quantitative fashion, this sensor can be used to measure the NO in asthma patients. Ideally, such a conversion module should hold for a number of months or even years, be cost-effective and convert the NO into $NO_2$ at the highest conversion rate, which is as constant as possible. The challenge in optimizing the gas conversion is that, on the one hand, a long retention time of the gas in the arrangement for gas conversion improves the conversion rate and, on the other hand, already generated $NO_2$ is increasingly adsorbed in the arrangement for gas conversion in the case of a long retention time. Additionally, a long conversion path increases the respiratory resistance against which the patient must exhale. Since an excessive respiratory resistance is inadmissible for the measurement of the target gas (see: ATS/ERS Recommendations for Standardized Procedures for the Online and Offline Measurement of exhaled Lower Respiratory Nitric Oxide and Nasal Nitric Oxide, 2005; American Thoracic Society (ATS) and the European Respiratory Society (ERS)), an upper limit is prescribed hereby for the length of the conversion path.

A further problem lies in the fact that the conversion rate of an arrangement for gas conversion is not constant over the service life, but decreases with time. This leads to an error in determining the concentration of the initial gas.

SUMMARY

In at least one embodiment, a device and a method are provided.

At least one embodiment of the invention relates to a device for measuring at least one gas analyte in exhaled air by means of a gas sensor unit with at least one gas sensor, having an arrangement for gas conversion, wherein the arrangement for gas conversion has an effective cross section of greater than 0.01 cm² and less than 100 cm², and an effective volume of greater than 0.05 ml and less than 100 ml.

An "arrangement for gas conversion", a "(gas) conversion module" or "gas conversion arrangement" means any arrangement that conditions the exhaled respiratory gas or compounds contained therein in order to allow a measurement of the gas analyte, e.g. for drying the respiratory gas with a drying agent or for converting a gas analyte to be detected into another measureable product.

Effective sizes are understood to be the geometric dimensions adjusted by the component of the filler material of the gas conversion arrangement.

According to one embodiment, the invention relates to a device for measuring at least one gas analyte in the exhaled air, wherein the at least one gas analyte is nitrogen monoxide and the arrangement for gas conversion is an arrangement for oxidizing nitrogen monoxide to nitrogen dioxide.

According to one embodiment, the invention relates to a device for measuring at least one gas analyte in the exhaled air, wherein the arrangement for oxidizing nitrogen monoxide to nitrogen dioxide has an oxidizing agent. By way of example, said arrangement can be designed as a container or body through which the exhaled air can be passed, which container or body is filled or designed with the oxidizing agent, e.g. potassium permanganate.

According to one embodiment, the invention relates to a device for measuring at least one gas analyte in exhaled air, wherein the arrangement for oxidizing nitrogen monoxide to nitrogen dioxide has a catalyst for catalyzing the oxidation of nitrogen monoxide to nitrogen dioxide. By way of example, said arrangement can be designed as a container or body through which the exhaled air can be passed, which container or body is filled or designed with a substrate material (e.g. a porous ceramics material) with a catalyst coating (e.g. a precious metal catalyst, such as e.g. Pt or Rh).

According to one embodiment, the invention relates to a device for measuring at least one gas analyte in exhaled air, wherein the arrangement for gas conversion is provided as a consumable, e.g. in a separate unit. This can be embodied as e.g. a cartridge that can be replaced without relatively great complexity, that is to say e.g. without tools being necessary.

According to one embodiment, the invention relates to a device for measuring at least one gas analyte in exhaled air, wherein the arrangement for gas conversion has a cross section of 0.5-2 $cm^2$ and a length of approximately 0.2-1 cm, more particularly a cross section of 1 $cm^2$ and a length of 0.6 cm and preferably has a cylindrical, prism, or cuboid design.

According to one embodiment, the invention relates to a device for measuring at least one gas analyte in exhaled air, comprising means for determining a conversion rate of the arrangement for gas conversion, which conversion rate is corrected in respect of the usage state of the arrangement for gas conversion.

The conversion rate can be expressed as a factor q, which describes the relation between the concentration of the initial analyte c[analyte] and the product c[product] measured by the sensor as follows:

$$c[product]=q*c[analyte].$$

Ideally, q=100% or q=1, but in reality q is less than 1 because not 100% of the analyte is converted into the product. Since the arrangement for gas conversion can be used up during usage, the conversion rate changes as a function of the usage state of the gas conversion arrangement. Thus, q is a function f of the usage state G, and so $$q=f(G)$$

holds true. The usage state G is a measure of the amount that the gas conversion arrangement has already been in use at any given time, and can be recorded quantitatively, for example in the form of the total volume of respiratory gas that has flown through the gas conversion arrangement, or approximately with the aid of the number of usage cycles of the arrangement for gas conversion that have been run through. For this purpose, the assumption can for example be made that on average the same amount of gas is exhaled during the measurement procedure in each usage cycle by the subject or patient.

This change in the conversion rate as a function of the usage state also holds true for the use of a catalyst in the gas conversion arrangement, which catalyst can also deteriorate over time, for example by clogging of the pores in the substrate material or by decomposition of the catalyst, in the case of metal catalysts due to e.g. oxidation, formation of the metal sulfide and similar reasons.

According to one embodiment, the invention relates to a device for measuring at least one gas analyte in exhaled air, wherein the means for correcting the conversion rate comprises the following features:

means for determining the usage state of the arrangement for gas conversion and means for calculating the corrected conversion rate with the aid of the usage state.

Provision can optionally be made for a storage arrangement for storing the usage state of the arrangement for gas conversion.

According to one embodiment, the invention relates to a device for measuring at least one gas analyte in exhaled air, wherein the means for determining the usage state of the arrangement for gas conversion comprises a flow sensor for determining a gas volume flowing through the arrangement for gas conversion, wherein the usage state is measured with the aid of the overall volume of gas that has flown through the arrangement for gas conversion at any given time.

According to one embodiment, the invention relates to a device for measuring at least one gas analyte in exhaled air, wherein the means for determining the usage state of the arrangement for gas conversion comprises means for counting the usage cycles of the device or the gas conversion arrangement, wherein the usage state is measured with the aid of the overall number of usage cycles that the device has passed through at any given time.

According to one embodiment, the invention relates to a device for measuring at least one gas analyte in exhaled air, wherein the means for calculating the corrected conversion rate has a computational arrangement for calculating the corrected conversion rate with the aid of the usage state, which computational arrangement is suitable for calculating the corrected conversion rate as a function of the usage state or with the aid of stored or entered correction factors, wherein the correction factor to be used is correlated to the usage state.

These correction factors to be stored or entered can for example be established by the producer in simple trial runs and be provided to the user as e.g. a table. They can likewise be stored in the device in an electronic storage arrangement and can be taken into account during the calculation and the display of the measurement parameter.

In order to establish the correction factors or a correction function, the gas conversion arrangement is actuated with a defined volume of a reference gas with a known initial concentration of the analyte over a multiplicity of usage cycles, e.g. 2, 5, 10, 100 or 1000, and the concentration of the conversion product being created is subsequently measured. Correction factors or a correction function can be determined with the aid of the now known number of usage cycles or the known overall volume of the reference gas.

According to a further embodiment, the invention relates to a device for measuring at least one gas analyte in exhaled air, wherein the means for correcting the conversion rate additionally comprises the following features:

a first and a second gas conversion arrangement with differing volumes V1 and V2, respectively, wherein different concentrations c1 and c2 are measured after conversion in the case of identical initial concentrations of the gas analyte to be measured, wherein c2=q'*c1 holds true, wherein q' changes as a function of the usage state and can be used for calculating a corrected conversion rate with the aid of stored or entered correction factors or with the aid of a function f' of the usage state G according to q'=f'(G).

According to a further embodiment, the invention furthermore relates to a method for detecting a gas analyte in respiratory gas, comprising the following steps:

converting the gas analyte into a detectable product by a gas conversion arrangement, determining the concentration of the product, establishing a conversion rate of the gas conversion arrangement, establishing the concentration of the gas analyte with the aid of the conversion rate and the concentration of the detectable product.

Assuming that the conversion rate q is constant then allows q to be used as a constant factor for calculating the initial concentration of the gas analyte for each gas conversion arrangement.

According to one embodiment, the invention relates to a method for detecting a gas analyte, wherein a corrected conversion rate is established as a function of the usage state of the gas conversion arrangement.

According to one embodiment, the invention relates to a method for detecting a gas analyte, wherein the usage state is measured with the aid of the entire volume of gas that, at any given time, has flown through the arrangement for gas conversion.

According to one embodiment, the invention relates to a method for detecting a gas analyte, wherein the usage state is measured with the aid of the overall number of usage cycles that the device has passed through at any given time.

According to one embodiment, the invention relates to a method for detecting a gas analyte, wherein the corrected conversion rate is calculated as a function of the usage state or with the aid of a stored or entered correction factor, wherein the correction factor to be used correlates with the usage state.

According to one embodiment, the invention relates to a method for detecting a gas analyte, wherein calculating the corrected conversion rate additionally comprises the following steps:

measuring two different concentrations $c_1$ and $c_2$ by a first and a second gas conversion arrangement with differing volumes $V_1$ and $V_2$, respectively, with an identical initial concentration of the gas analyte to be measured, wherein $c_2 = q'*c_1$ holds true, wherein the factor $q'$ changes as a function of the usage state and calculating the corrected conversion rate as a function of the factor $q'$ or with the aid of a stored or entered factor $q'$.

It is preferable for the gas analyte to be NO, the product of the gas conversion to be $NO_2$, and the gas sensor to be an $NO_2$-sensitive FET sensor.

The oxidation can be brought about by passing the (respiratory) air through an oxidizing agent (e.g. potassium permanganate, perchlorate salts or the like) or an oxidation catalyst (e.g. a precious metal catalyst, photocatalyst or the like).

In order to keep the concentration losses of the converted gas at the column exit to a minimum as a result of setting a chemical equilibrium, the invention proposes that the conversion module is inserted through an externally accessible shaft directly in front of or within the measurement chamber such that the converted gas can be measured soon after the conversion.

In this embodiment, the conversion module advantageously is situated behind a valve in the flow-channel system, and so the conversion module is not subjected to environmental effects when the valve is closed (e.g. in the passive, unused state of the measurement instrument), and hence the service life is increased.

In another embodiment, the conversion module is embodied such that e.g. a change in color or another noticeable change shows when the module has been used up and needs to be replaced. A comparison color scale can be attached next to the window for observing the change in color. The change in color can thus also be used for establishing the usage state for calculating the corrected conversion rate. This constitutes a particularly simple and cost-effective embodiment of the invention.

The conversion rate of a conversion mediator, which is being used up, such as e.g. potassium permanganate, systematically decreases with time and can also be subject to variations, e.g. as a result of a varying surrounding temperature. An error in the conversion rate leads directly to a measurement error of the target gas concentration.

In order to correct such random or systematic changes in the conversion rate, the following optional features are proposed:

The systematic change in the conversion rate as a result of using up a conversion agent is directly related to the amount of gas that has flown through the module. Thus, the invention proposes to measure by integration the amount of gas that has flown through the module over many application cycles, and to store this value in a memory chip. Alternatively, it is also possible to estimate the amount of gas by adding and storing the number of measurement cycles if the assumption is made that the amount of gas is approximately the same in each respiratory cycle. Using the gas flow values determined in this fashion, a correction value is then determined from a correction table determined by the producer and stored in the instrument (or by means of a correction function) and the currently measured conversion rate or the currently measured product concentration is corrected with the aid of this correction value.

The change in the conversion rate is determined by two independent measured values from two different conversion columns in the instrument, and the measured value of the concentration of the target gas is corrected thereby. This method assumes that the ageing effect on the conversion agent in different column volumes is unequal, for example that a column with a small volume $V_1$ ages more quickly than a column with a larger volume $V_2$.

Such an arrangement for determining the conversion rate change by metrology is described in an exemplary fashion in the attached FIG. 3.

As per one embodiment of the invention, the gas sensor unit has an $NO_2$-sensitive field-effect transistor sensor (FET sensor).

BRIEF DESCRIPTION OF THE DRAWINGS

Hereinbelow, the invention will be described with the aid of examples and in conjunction with the figures, in which.

DETAILED DESCRIPTION OF THE EXAMPLE EMBODIMENTS

Figure 1:
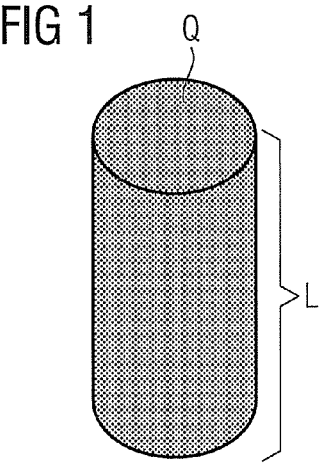
FIG. 1 shows a schematic illustration of a gas conversion module for use in the device according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The present example relates to a measurement instrument for determining the NO content in the exhaled air of a patient or subject. The arrangement for gas conversion in this case is used to oxidize NO to $NO_2$. However, this embodiment should only be considered to be exemplary; the invention is likewise suitable to be used for detecting other gas analytes.

FIG. 1 shows, in an exemplary and schematic fashion, an arrangement for gas conversion designed as a gas conversion module for use in the device according to the invention, which has a cylindrical embodiment of the column with a cross section Q of approximately 1 $cm^2$ and a length L of approximately 0.6 cm.

The gas conversion module can have an outer column body suitable for holding an open-pore, powdery, fiber-like or otherwise gas-permeable filler material. The filler material can be e.g. an oxidizing agent (e.g. potassium permanganate) or another oxidation catalyst (e.g. Pt) on an open-pore substrate material.

Figure 2:
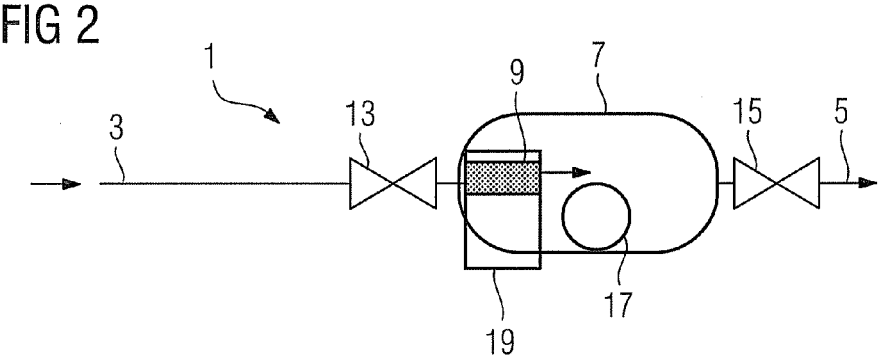
FIG. 2 shows a schematic illustration of an embodiment of the device according to the invention.

FIG. 2 shows a first embodiment of the device 1 according to the invention with an inlet opening 3 (embodied e.g. as a mouthpiece), a measurement chamber 7 with a gas conversion arrangement 9 and a gas sensor unit 17. The gas conversion arrangement 9 is provided in a cutout provided therefor or in a shaft 19 and can be replaced manually in a simple fashion by means of e.g. a plug-in connection. The exhaled air leaves the instrument via an outlet opening 5. An inlet valve 13 and an outlet valve 15 can be used to control the gas flow and gas can be locked into the measurement chamber for the measurement. The gas conversion module 9 can be designed to be reusable, or as a consumable or as a single-use article, which can be removed from the instrument and regenerated or disposed of after being used up.

The gas conversion arrangement 9 converts the gas analyte into a product whose concentration can be measured by the sensor 17.

The valve 13 and/or 15 can optionally be designed as a one-way valve (e.g. as a check one-way valve) (not illustrated), and so the user can no longer suck in and once again breathe in air once it has been exhaled into the instrument.

The gas conversion arrangement 9 can be designed such that e.g. a change in color or another perceivable change is displayed once the module has been used up and needs to be replaced. A comparison color scale can be attached next to the window for observing the change in color or the usage state (not illustrated). Corresponding correction factors for calculating the corrected conversion rate can be specified on the color scale. These can be specified as e.g. percentage points, and so the initial concentration of the gas analyte can be determined directly from the measured concentration of the product.

Alternatively, for determining the usage state, provision can be made for e.g. a flow sensor (e.g. an impeller flow wheel) to determine the gas volume that has flown past it or for a counter to count the usage cycles.

Provision can also be made for an electronic data processing arrangement that calculates the initial concentration directly with the aid of the measured concentration of the product and the usage state.

Correction values or a correction function can be predefined by the producer.

Furthermore, provision can be made for a temperature sensor for measuring the temperature of the gas conversion arrangement such that the conversion rate can also be corrected in respect of the temperature.

Furthermore, provision can be made for a heating device such that the gas conversion arrangement can be brought to an optimum temperature at which there is a maximum conversion rate.

Moreover, the device can optionally have a data processing arrangement for calculating the corrected conversion rate.

By way of example, the use of an $NO_2$-sensitive sensor on the basis of a transistor is conceivable as a gas sensor 17. Various field-effect transistors are known for nitric oxide detection according to the output work measurement principle, in which a gate electrode constitutes the gas-sensitive layer. This gate electrode can be separated from the so-called channel region of the field-effect transistor by an air gap. The basis for a detecting measurement signal is the change in the potential between gate and channel region ($\Delta V_G$). By way of example, in the German patent applications No. 198 14 857.7 and No. 199 56 806.5, the entire contents of each of which is hereby incorporated herein by reference, hybrid flip-chip structures of gas sensors are described, which are designed as CMOS transistors. Moreover, a gas sensor can be equipped with two field-effect transistors, the control behavior of which is matched by air gaps of approximately the same size between the channel region and gate electrode, and whose sensor layers can be read out separately. The German patent application No. 199 56 744.1, the entire contents of which is hereby incorporated herein by reference, describes how the spacing between gate electrode and channel region in a field-effect transistor can be implemented in a reproducible fashion by very precise spacers. Another refinement provides for the gas-sensitive material to be applied to the channel region or the gate in a porous form.

Gas-sensitive layers for use in a so-called SG-FET (suspended gate field-effect transistor) can advantageously be porphin dyes, such as phthalocyanines with a copper or lead central atom. In the case of sensor temperatures between 50° C. and 120° C., nitric oxide sensitivities can be detected down to the lower ppb range. The detection is targeted at nitrogen dioxide, as usual.

Other materials suitable for use as gas-sensitive layers in gas-sensitive field-effect transistors for detecting nitric oxide, more particularly nitrogen dioxide, are fine-crystalline metal oxides operated at temperatures between 80° C. and 150° C. More particularly, these can be $SnO_2$, $WO_3$ or $In_2O_3$; carbonate salts such as barium carbonate or polymers such as polysiloxanes are likewise feasible.

In a further embodiment of the invention, the device 1 additionally contains a particulate filter (not illustrated) in order to avoid a contamination of the measurement instrument by bacteria. By way of example, appropriate HEPA (high efficiency particulate air) filters are suitable. The filter should have sufficiently fine pores to filter bacteria, viruses or similar contaminants from the air stream, but at the same time offer a low flow resistance.

According to a further embodiment (not illustrated), the gas conversion arrangement is integrated in the sensor element itself (hybrid or monolithic). This can be brought about by a multi-layered design (e.g. oxidation catalyst layer, sensor layer) or by a monolithic design (the sensor surface is on the same substrate body and is mixed, homogeneously or heterogeneously, with the catalytically active material and an optional dehumidifying agent).

In one embodiment, the device is actuated upon by a calibrating gas with a defined analyte concentration in selectable time intervals for quality control or calibration purposes. This calibration process can also be used to verify the effective rate of the conversion module and to activate the regeneration in the case of decreasing effective rate.

Figure 3:
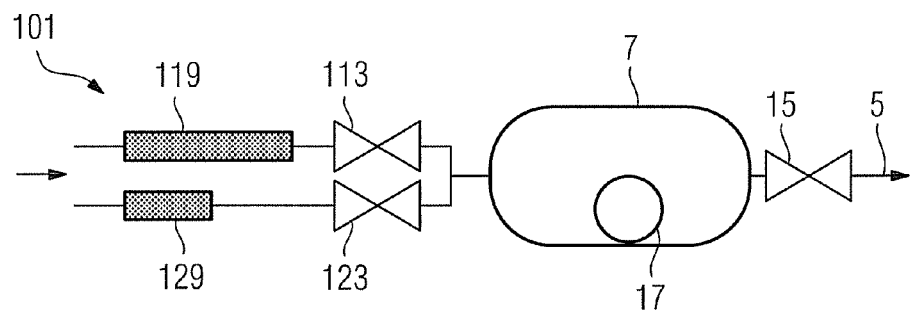
FIG. 3 shows a schematic illustration of a further embodiment of the device according to the invention.

According to a further embodiment, FIG. 3 shows a device 101 according to the invention with a measurement chamber 7 and with two gas conversion arrangements 119 and 129 with valves 113 and 123.

The two gas conversion modules have different volumes V1 and V2, with it being intended in this example that V1>V2 holds true. The gas flow is controlled by the valves 113, 123 such that the two gas flows are measured with a time offset. By way of example, this is achieved by virtue of the fact that the two flow paths are opened and closed alternately, or by virtue of the fact that the gas flow from the gas conversion arrangement 129 reaches the sensor earlier than that from the gas conversion arrangement 119 as a result of suitable flow paths. Therefore, the sensor measures two gas concentrations c2 and c1 at different times. In the unused state, a relation (that can be determined by metrology) holds true between the two measured values: c2=q'*c1. The larger concentration value c1 results from the fact that the conversion rate of the column with V1 is greater than that with V2 and thus a larger amount of the converted product arrives at the sensor. The constant q' would remain unchanged over many measurement cycles if the gas conversion arrangement would not be used up. However, the constant q' changes as a function of usage in the case of a gas conversion arrangement that is being used up. Thus, the constant q' can be used to determine a correction value from a correction table, determined by the producer and stored in the instrument, (or by means of a correction function) and to correct the currently measured conversion rate or the currently measured target gas concentration using this correction value. Furthermore, a change in the constant can be used to make the user aware of the fact that the gas conversion arrangement needs to be replaced, particularly if it is designed as a consumable.

Using the described methods affords the possibility of generating a message relating to the progress of the service life of the gas conversion arrangement once a fixed amount of gas has been exceeded. This message can be transmitted to the user as e.g. a request to replace the module.

An expedient boundary value for the overall amount of gas after which the converter needs to be replaced can result from the reliability of the converter having dropped so much that the required accuracy of the measurement result is no longer ensured.

The device and the method of embodiments of the invention enable a simple and robust measurement instrument that allows reliable determination of the concentration of the analyte.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An improvement for a gas sensor device operable for measuring nitrogen monoxide in exhaled air, the device including a measurement chamber including an inlet for receiving a gas in communication with the measurement chamber and a gas sensor unit disposed within the chamber and including at least one gas sensor, comprising:
an arrangement for gas conversion in fluid communication between the inlet and the at least one gas sensor and configured to convert the nitrogen monoxide in the exhaled air to nitrogen dioxide measured by the gas sensor device, wherein the arrangement for gas conversion includes an effective cross section of greater than $0.01$ $cm^2$ and less than $100$ $cm^2$, and includes an effective volume of greater than 0.05 ml and less than 100 ml; and
means for determining a conversion rate of the arrangement for gas conversion and correcting the conversion rate in respect of a usage state of the arrangement for gas conversion.

2. The improvement as claimed in claim 1, wherein the arrangement for gas conversion includes an oxidizing agent.

3. The improvement as claimed in claim 1, wherein the arrangement for gas conversion includes a catalyst for catalyzing the oxidation of nitrogen monoxide to nitrogen dioxide.

4. The improvement as claimed in claim 1, wherein the arrangement for gas conversion is provided as a consumable.

5. The improvement as claimed in claim 1, wherein the arrangement for gas conversion is provided in a separate replaceable unit from the gas sensor unit.

6. The improvement as claimed in claim 1, wherein the arrangement for gas conversion includes a cylindrical design with a cross section of $0.5$-$2$ $cm^2$ and a length of approximately 0.2-1 cm.

7. The improvement as claimed in claim 1, wherein the means for determining and correcting a conversion rate comprises:
means for determining the usage state of the arrangement for gas conversion and means for calculating the corrected conversion rate with the aid of the usage state.

8. The improvement as claimed in claim 7, wherein the means for determining the usage state of the arrangement for gas conversion comprises a flow sensor for determining a gas volume flowing through the arrangement for gas conversion, wherein the usage state is measured with the aid of the overall volume of gas that has flowed through the arrangement for gas conversion at any given time.

9. The device as claimed in claim 7, wherein the means for determining the usage state of the arrangement for gas conversion comprises means for counting the usage cycles of the device, wherein the usage state is measured with the aid of the overall number of usage cycles that the device has passed through at any given time.

10. The improvement as claimed in claim 7, wherein the means for calculating the corrected conversion rate has a computational arrangement for calculating the corrected conversion rate with the aid of the usage state, which computational arrangement is configured for calculating the corrected conversion rate as a function of the usage state or with the aid of stored or entered correction factors, wherein one correction factor of said correction factors to be used is correlated to the usage state.

11. The improvement as claimed in claim 10, wherein:
the arrangement for gas conversion includes a first and a second gas conversion arrangement with differing volumes V1 and V2, respectively, and
the means for determining and correcting the conversion rate additionally measures different concentrations c1 and c2 after conversion of identical initial concentrations of the gas analyte by each of said first and second gas conversion arrangements, respectively, wherein $c2=q'*c1$ holds true, wherein q' changes as a function of the usage state and can be used for calculating a corrected conversion rate with the aid of stored or entered correction factors or a function of q'.

12. The improvement as claimed in claim 6, wherein the arrangement for gas conversion includes a cylindrical design with a cross section of $1$ $cm^2$ and a length of 0.6 cm.

13. The improvement of claim 5, wherein:
the inlet for receiving a gas is defined in the measurement chamber;
an enclosed shaft is provided between the gas sensor unit and the inlet; and
the arrangement for gas conversion is configured to be replaceably mounted within the enclosed shaft in fluid communication between the inlet and the gas sensor unit.

14. The improvement of claim 13, wherein the enclosed shaft is incorporated within the measurement chamber.

15. The improvement of claim 1 in which the device includes an inlet, further comprising a valve between the inlet of the device and the arrangement for gas conversion.

16. The improvement of claim 1, wherein the arrangement for gas conversion is configured to display a color indicative of the usage state thereof.

17. The improvement of claim 1, further comprising a temperature sensor associated with the measurement chamber, and wherein said means for determining and correcting a conversion rate is further configured to correct the conversion rate as a function of the temperature measured in the chamber.

18. The improvement of claim 1, further comprising a device for heating the arrangement for gas conversion to a temperature at which the arrangement produces a maximum gas conversion rate.

* * * * *